(12) United States Patent
Obradovic

(10) Patent No.: US 10,786,376 B2
(45) Date of Patent: Sep. 29, 2020

(54) EXPANDABLE VASCULAR STENT

(71) Applicant: Bentley InnoMed GmbH, Hechingen (DE)

(72) Inventor: Milisav Obradovic, Lorrach (DE)

(73) Assignee: Bentley InnoMed GmbH, Hechingen (DE)

(*) Notice: Subject to any disclaimer, the term of this patent is extended or adjusted under 35 U.S.C. 154(b) by 0 days.

(21) Appl. No.: 15/756,324

(22) PCT Filed: Sep. 9, 2016

(86) PCT No.: PCT/EP2016/071296
§ 371 (c)(1),
(2) Date: Feb. 28, 2018

(87) PCT Pub. No.: WO2017/042329
PCT Pub. Date: Mar. 16, 2017

(65) Prior Publication Data
US 2018/0256374 A1 Sep. 13, 2018

(30) Foreign Application Priority Data
Sep. 10, 2015 (DE) .......... 10 2015 115 279

(51) Int. Cl.
*A61F 2/915* (2013.01)

(52) U.S. Cl.
CPC ...... *A61F 2/915* (2013.01); *A61F 2002/9155* (2013.01); *A61F 2002/91558* (2013.01);
(Continued)

(58) Field of Classification Search
CPC ........ A61F 2/82–945; A61F 2250/0029; A61F 2230/0013
See application file for complete search history.

(56) References Cited

U.S. PATENT DOCUMENTS

2001/0044652 A1* 11/2001 Moore .............. A61F 2/91
623/1.16
2004/0133271 A1 7/2004 Jang
(Continued)

FOREIGN PATENT DOCUMENTS

DE 20221761 U1 8/2007
EP 2353551 B1 10/2016
(Continued)

OTHER PUBLICATIONS

Office Action dated Dec. 19, 2019 in connection with related Russian Patent Appl. No. 2018112503.
(Continued)

*Primary Examiner* — Rebecca S Preston
(74) *Attorney, Agent, or Firm* — Brooks Kushman P.C.

(57) ABSTRACT

Vascular stent, in particular made of an in vivo degradable plastic material, having individual ring segments (2), the webs (4) of which are of meandering configuration, and comprising connecting webs (3) arranged between adjacent ring segments (2), said webs converging in connection points (7) with the webs (4) of the ring segments (2), with recesses (9a, 9b) being arranged at angles of the connection points (7) that are compressed when the vascular stent (1) is expanded, said recesses being open towards the edge and extending through the ring segment webs (4) and connecting webs (3), with a view to reducing stresses arising during the expansion of the vascular stent (1).

13 Claims, 3 Drawing Sheets

(52) U.S. Cl.
CPC ............... *A61F 2002/91566* (2013.01); *A61F 2002/91575* (2013.01); *A61F 2210/0004* (2013.01); *A61F 2230/0006* (2013.01); *A61F 2230/0013* (2013.01); *A61F 2250/0012* (2013.01); *A61F 2250/0036* (2013.01); *A61F 2250/0071* (2013.01)

(56) References Cited

U.S. PATENT DOCUMENTS

| | | | |
|---|---|---|---|
| 2006/0271170 A1* | 11/2006 | Gale | ................. A61F 2/91 623/1.49 |
| 2007/0168010 A1 | 7/2007 | Goshgarian | |
| 2009/0254173 A1 | 10/2009 | Jang | |
| 2014/0025161 A1 | 1/2014 | Stankus et al. | |
| 2014/0277401 A1 | 9/2014 | McClain et al. | |

FOREIGN PATENT DOCUMENTS

| | | |
|---|---|---|
| JP | 2007512114 | 5/2007 |
| JP | 2009101068 | 5/2009 |
| RU | 2349290 C1 | 3/2009 |
| RU | 2506933 C2 | 2/2014 |
| WO | WO2003/047463 A1 | 6/2003 |

OTHER PUBLICATIONS

Office Action dated May 12, 2020 in connection with related Brazilian Patent Appl. No. BR112018003340.5.
Office Action dated Jun. 23, 2020 in connection with related Japanese Patent Appl. No. 2018-511449.

* cited by examiner

EXPANDABLE VASCULAR STENT

The invention relates to a vascular stent or vessel support having individual ring segments, the webs of which are of a meandering configuration, and comprising connecting webs arranged between adjacent ring segments said webs converging in connection points with the webs of the ring segments. In particular, the vascular stents or vessel supports consist of a material that can decompose in vivo and, especially preferred, are made of a plastic material having these properties.

Vascular stents are often used in the coronary, cerebral and peripheral areas to expand and recanalize narrowed vessels and to seal off aneurysms, shunts and undesirable branches in vessels. In this context, materials capable of decomposing in vivo, which dissolve in the body over a defined period of time, are increasingly being used. Vessel supports, in particular drug-coated/eluting stents, are usually needed for a limited period of time only and are no longer of use when they have fulfilled their purpose.

With a view to obtaining such in vivo degradable vascular stents, a large number of materials was tested, both of metallic nature and on plastic basis. In the case of metals, magnesium alloys have proved particularly useful. Among the plastic materials, vascular stents based on polylactides and polyglycolides have inter alia been developed.

Vascular stents serving the purpose of widening vessels are usually crimped onto balloons and placed in position by means of catheters and then expanded with the help of said balloons, following which the balloons are withdrawn in a deactivated state leaving the vascular stent at the placement site. During the expansion of the vascular stents, individual ring segments are widened to a greater or lesser extent causing them to come under tension. However, such widening also causes the parts of the stent that are under tension to move out of the cylinder plane with the result that edges and fins develop that might lead to vessel injuries.

This danger can at least in part be counteracted by using plastic materials. Plastics are less hard than metals and have less tendency to form sharp edges. However, a disadvantage of plastic stents is their tendency to form cracks during expansion in areas stressed by tension or to buckle severely when subjected to compression. Especially in the case of vascular stents, which consist of a plurality of ring segments with meandering webs, this behavior is frequently encountered. On the other hand, stent structures of this kind have been successfully employed as a result of their radial behavior and due to the controllability of their length reduction during expansion.

In view of this, it is the objective of the present invention to provide structures by means of which the tensions described hereinbefore as they occur during the expansion of a vascular stent are reduced. This does not only apply to the particularly affected stents of plastic material, but also to stents made of metallic materials, whether they are degradable in vivo or not.

This objective is achieved by means of a vascular stent of the kind first mentioned above, in which recesses are arranged at angles of connection points being compressed when the vascular stent is expanded, said recesses being open towards the edge and extending through the ring and connecting webs, with a view to reducing stresses occurring during the expansion of the vascular stent (1).

Within the meaning of the invention, the terms "stent", "vascular stent" and "vessel support" are used synonymously herein. The terms do not only refer to vascular and coronary stents, but rather to all vessel supports that can be inserted and placed into body lumina.

The term "ring segment" refers to supporting elements of a vessel support which extend in the circumferential direction. Such ring segments have a meandering configuration so that the diameter of the vascular stent can be enlarged by stretching the loops during expansion. "Meandering" in this context refers to a configuration with bends, in serpentine lines or zigzag shape.

Depending on viewpoint, the individual ring segments of a vessel support consist of a single web of curved extension or a multitude of webs, which are connected to each other thus forming the meandering pattern.

Adjoining ring segments of a vessel support are attached to each other by connecting webs. Connecting webs can have a straight, curved, S-shaped or spiral shape; preferred according to the invention are connecting webs having a straight configuration.

It is desirable as a rule to limit the longitudinal contraction of a stent during expansion. In the event curved connecting webs are provided, this is achieved by stretching the webs, and when using straight connecting webs by arranging them between the outer arches of a ring segment and the inner arches of the adjacent ring segment. The connecting webs are thus arranged between the respective arches of adjacent meanders, on the one hand on the outside and on the other hand on the inside.

The webs of the ring segments on the one hand and the connecting webs on the other meet on both ends of the connecting webs thus forming connection points. In the configuration described above, three web arms originate at each of the connection points.

As proposed by the invention, there are recesses at some of the connection points that extend into the web from the outside, preferably at the connection points where the ring segments are compressed or upset in the area of the junction points of the connecting webs. This is usually the case with the connection points at the outer arches. The recesses give the compressed material of the ring segment space to move to the side, so that the above described bulges do not occur.

The recesses can be provided in the form of notches or incisions that lead into and through the web from the outside, but can also be regular cutouts or "punchings". Preferably, the recesses have a rounded contour, which offers advantages in that incipient cracks that may be encountered when crimping on a balloon and expanding the balloon are eliminated. Particularly preferred are recesses having a circular or elliptical contour. The recesses extend through the web and are open towards the edge or rim.

In the area of the angles of the connection points, the recesses extend from the edge into the ring segment webs and also cover the connecting webs. In the event of circular or elliptical recesses, the radius preferably ranges between $\frac{1}{20}$ and $\frac{1}{10}$ of the web width. The same applies analogously for incisions and notches.

Alternatively or additionally, the webs of the ring segments may be provided with incisions in the area of the arches of the meandering ring segments. The incisions are provided in the form of slots that follow the course of the ring segment, with said incisions or slots being arranged completely in the interior of the webs. Preferably, their width amounts to between $\frac{1}{40}$ and $\frac{1}{4}$, in particular between $\frac{1}{20}$ and $\frac{1}{10}$ of the web width. The incisions provide flexibility to the ring segments and are suitable for accommodating the material displaced during compression.

The incisions or slots are preferably arranged in the area of the connection points of the ring segments in places where the connecting webs adjoin the inner arches. In this location, the ring segments on the side opposite to the connecting webs are provided with an indentation or depression, the contour of which is followed by the incisions.

Usually, the incisions extend over a length that corresponds to the single to triple web width.

In particular, incisions or slots may also be arranged in the area of the arches of the ring segments, where they follow the course of the web.

The inventive design of the vessel supports is particularly suitable for stents that are cut from a plastic material, for example a degradable plastic. As such, polylactides, polyglycolides, their copolymers and blends are particularly suitable. However, it is to be understood that the invention relates to vessel supports made of any material; it does not matter which material is used for the stents.

The stents proposed by the invention are customary balloon-expandable stents of the kind crimped onto a balloon in the usual manner, brought to the placement site by means of a balloon catheter and are hydraulically expanded, following which the catheter is retracted with the balloon in deflated state. It goes without saying that the stent can be coated or impregnated with active agents in a manner that is known per se, for example, to prevent restenosis in the case of narrowed vessels.

The invention is explained in more detail by way of the enclosed figures, where

Figure 1:
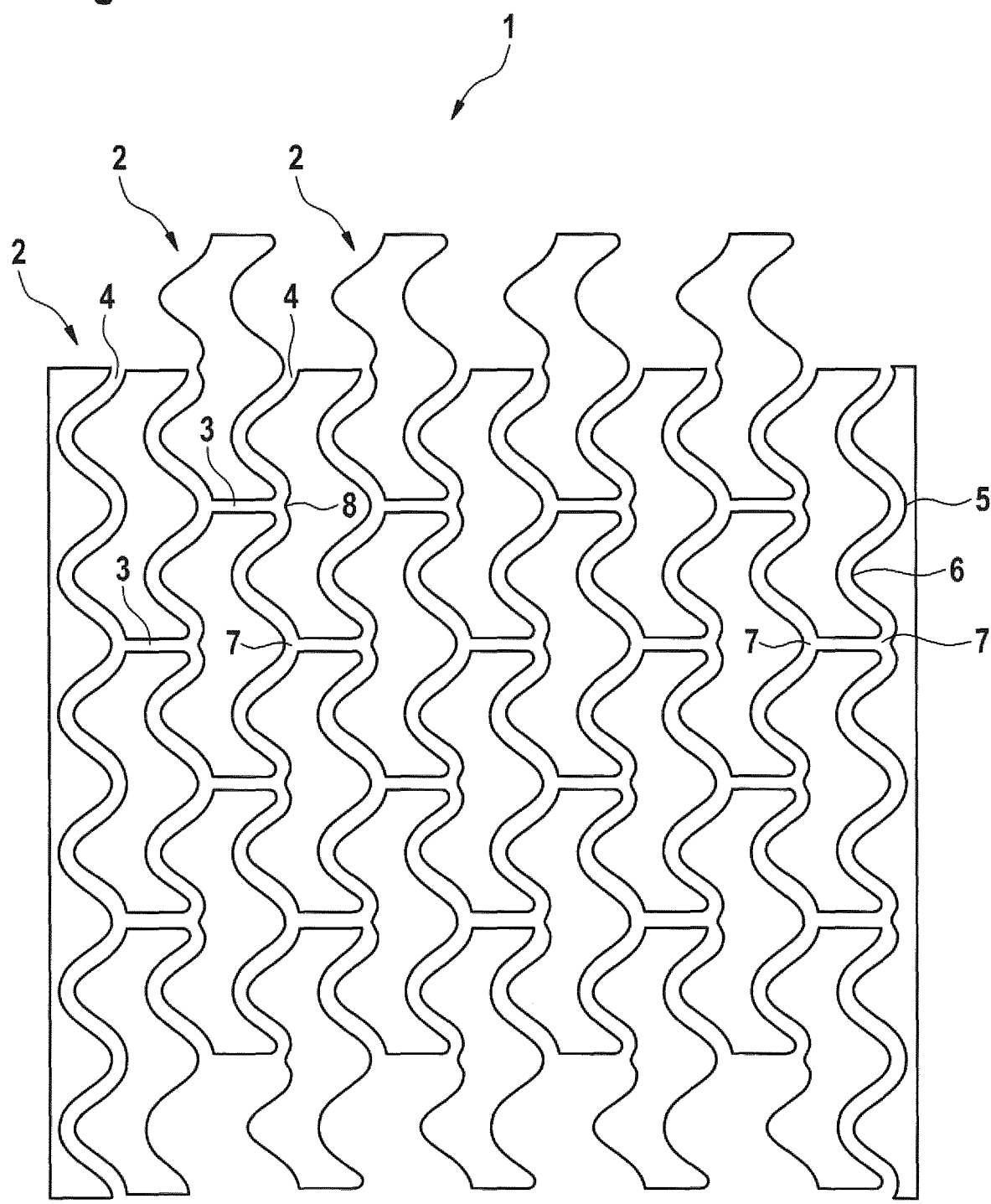
FIG. 1 shows a customary stent design in spread-out form.

In FIG. 1 a customary stent 1 is shown with meandering ring segments 2 and connecting webs 3 arranged between adjacent ring segments 2 in a cut and spread-out form. The individual ring segments consist of a continuous web 4, which follows a meandering or serpentine course, with outer arches 5, inner arches 6 and connection points 7 at connecting webs 3. The inner arches 6 at the connection points 7 of the connecting webs 3 have a trough-shaped depression 8. The width of the connecting webs 3 is slightly smaller than the web width of ring segments 2, by about 5 to 20%.

Figure 2:
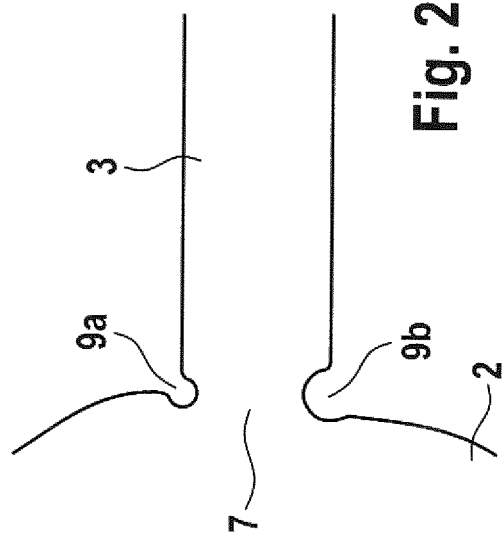
FIG. 2 is a partial section of the stent design shown in FIG. 1, which has been modified in accordance with the invention.

FIG. 2 shows a detail of the stent design depicted in FIG. 1 illustrating inventive recesses 9a and 9b. The recesses 9a and 9b are two independent variants, each of which can be realized individually, said recesses being arranged in the angles of connection point 7 between ring segment 2 and connecting web 3. Both recesses 9a and 9b have a circular contour and are shaped to form a rounded transition merging into the edges of ring segment 2 and connecting web 3. Both recesses 9a and 9b are arranged in such a way that they cover both connecting web 3 and ring segment 2, with recess 9b having a larger diameter than recess 9a.

Figure 3:
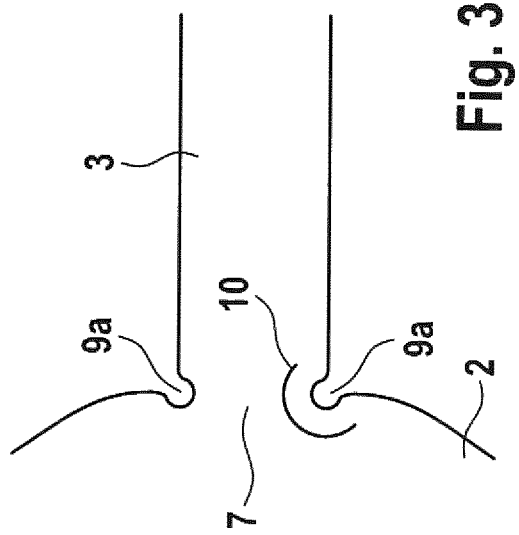
FIG. 3 shows modifications of the design shown in FIG. 2 with respect to recesses and incisions.

FIG. 3 shows another variant with respect to the design of connection points 7 with recesses 9a arranged in the angles formed between connecting webs 3 and ring segment 2. Around one of the recesses 9a an incision 10 is arranged, which is of almost semicircular shape and surrounds the recess 9a.

The recesses 9a and 9b shown in FIGS. 1 and 2 as well as incision 10 are located in areas of the stent 1 that are subjected to compressive stress during expansion. Through the recesses, free space is created into which material can be displaced during the expansion process, see FIGS. 6/7, and, moreover, the rounded contours of the recesses are conducive to preventing crack formation.

Figure 4:
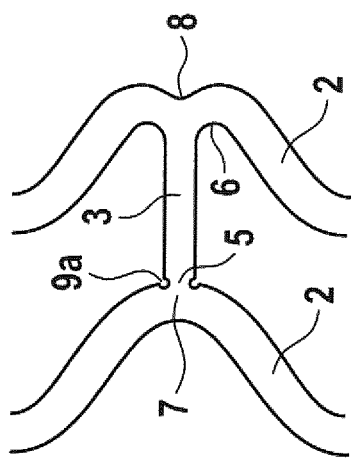
FIG. 4 illustrates further modifications of the design shown in FIG. 2.

FIG. 4 shows a further embodiment of an inventive stent with recesses 9a arranged in connection point 7. The connecting web 3 extends from the outer arch 5, which also represents connection point 7, to the inner arch 6 of the adjacent ring segment 2. At the place opposite to the web 3 and the inner arch 6, the ring segment 2 is provided with a depression or trough 8. As a result of such a trough-like formation, the inner arch 6 is elongated and allows a smoother rounding of the transition from connecting web 3 to ring segment 2.

Figure 5:
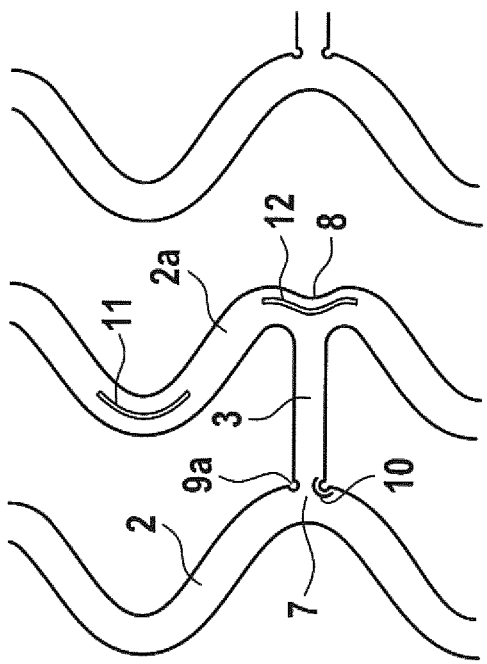
FIG. 5 depicts further modifications of the design shown in FIG. 2 including incisions.

In FIG. 5 another embodiment variant of a stent 1 is shown as proposed by the invention in the area of a connecting web 3 located between two ring segments 2. Recesses 9a in the area of the connection point can be surrounded by a semi-circular slot 10. Moreover, slit-shaped incisions 11 and 12, which follow the course of ring segment 2, are located on ring segment 2a which is arranged adjacent to ring segment 2 provided with the recesses 9a. Said slots are suitable to balance out the stresses arising during the expansion of the stent.

Figure 6:
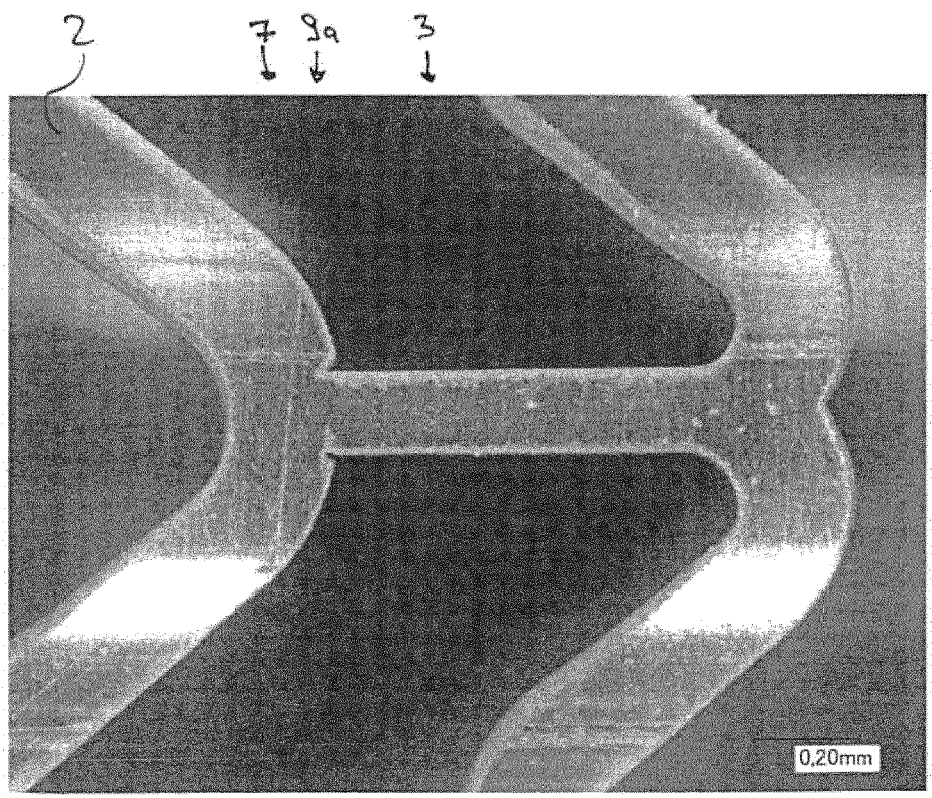
FIG. 6 is a photographic representation of a sample according to FIG. 2 before the stent is expanded.

FIG. 6 shows a photographic representation of a stent section comprising to recesses 9a in the area of connection point 7 between ring segment 2 and web 3.

Figure 7:
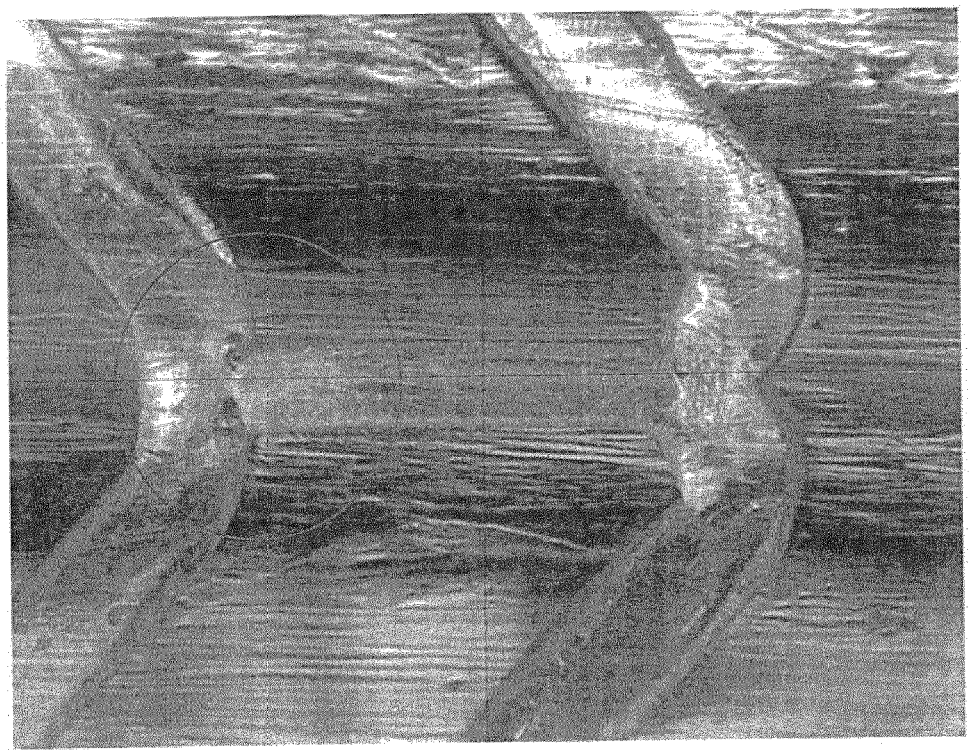
FIG. 7 shows the section of FIG. 6 after the stent has been expanded.

FIG. 7 is a representation of the same area of the stent shown in FIG. 6 after the expansion of the stent; the recesses have been closed as a result of material being displaced from ring segment 2.

It goes without saying that the characteristics shown in the figures and explained by way of the description shall in each case be regarded individually but they may as well be applied in other contexts. Accordingly, optional combinations of incisions and/or recesses may be provided in a stent. Vessel supports that are only provided with recesses in the area of the connection points, as well as stents that exclusively have incisions or slots in the area of the web configurations, thus fall within the scope of the invention as well.

The invention claimed is:

1. Vascular stent, in particular made of an in vivo degradable plastic material, having webs (4) of individual ring segments (2), the ring segment webs (4) being of meandering configuration, the stent comprising connecting webs (3) arranged between adjacent ring segments (2), said connecting webs (3) converging in connection points (7) with the ring segment webs (4), wherein recesses (9a, 9b) are arranged at angles of the connection points (7), the recesses (9a, 9b) having rounded corners and being compressed when the vascular stent (1) is expanded, said recesses being open extending through the ring segment webs (4) and connecting webs (3), with a view to reducing stresses arising during the expansion of the vascular stent (1); and wherein the recesses (9a, 9b) are located between the ring segments (2) and connecting webs (3), characterized in that incisions (10) extend through the ring segments and connecting webs (4, 3) and are arranged semicircularly around the recesses (9a, 9b), the incisions being of semicircular shape.

2. Vascular stent according to claim 1, characterized in that the recesses (9a, 9b) have an essentially circular or elliptical form.

3. Vascular stent according to claim 2, characterized in that the recesses (9a, 9b) have a radius ranging between 1/20 and 1/10 of the web width of the ring segments.

4. Vascular stent according to claim 1, characterized in that the incisions (10) are arranged in regions that are compressed during the expansion of the vascular stent.

5. Vascular stent according to claim 1, characterized in that the incisions (10) are arranged adjacent the connecting points (7).

6. Vascular stent according to claim 1, characterized in that the ring segments (2) have arches and slit-shaped incisions (11) are arranged through the arches of the ring segments (2).

7. Vascular stent according to claim 1, characterized in that the incisions (10) are slots having a width of 1/40 to 1/4 of the respective web width.

8. Vascular stent according to claim 1, characterized in that the ring segments (2) have inner and outer arches and the connecting webs (3) connect the outer arches of ring segments (2) with the inner arches of adjacent ring segments (2).

9. Vascular stent according to claim 8, characterized in that the inner arches adjoining the connecting webs (3) are provided with a trough-like depression (8) in the location opposite the junction point.

10. Vascular stent according to claim 9, characterized in that slit-shaped incisions (12) follow the course of the trough-like depression (8).

11. Vascular stent according to claim 1, characterized in that said stent consists of a plastic material which can be degraded in vivo and is expandable by means of a balloon.

12. Vascular stent according to claim 11, characterized in that the vascular stent consists of polylactide, polyglycolide or blends or copolymers thereof.

13. Vascular stent according to claim 1, characterized in that the incisions (10) are slots having a width of 1/20 to 1/10 of the respective web width.

* * * * *